United States Patent [19]

Reetz et al.

[11] 4,419,296
[45] Dec. 6, 1983

[54] PREPARATION OF TERTIARY ALKYL CYANIDES

[75] Inventors: Manfred T. Reetz; Ioannis Chatziiosifidis, both of Marburg, Fed. Rep. of Germany

[73] Assignee: Bayer Aktiengesellschaft, Leverkusen, Fed. Rep. of Germany

[21] Appl. No.: 353,986

[22] Filed: Mar. 2, 1982

[30] Foreign Application Priority Data

Apr. 22, 1981 [DE] Fed. Rep. of Germany ....... 3115976

[51] Int. Cl.³ .......................................... C07C 120/04
[52] U.S. Cl. ................................. 260/464; 260/465.1; 260/465.7; 260/465.8 R
[58] Field of Search .............................. 260/464, 465.1

[56] References Cited

PUBLICATIONS

C. A. Chemical Substance Index, Q-Z, 12-31-81, p. 6434cs, 95, (1981).
C. A., 95, (1981), Goto et al.
Chemical Abstracts, vol. 96, No. 7, Feb. 15, (1982), pp. 580, 96:51862x, Reetz et al.
Angewandte Chemie, vol. 93, No. 12, (1981), pp. 1037, 1075–1076; Reetz et al.
Methoden Der Organischen Chemie, vol. VIII, (1952), pp. 293–294.
Chemical Reviews, vol. 42, (1948), pp. 189–283, Mowry.
J. Goto et al., "New Sensitive Derivatization Reagent for Liquid Chromatographic Separation of Hydroxyl Compounds", Chem. Pharm. Bull., 29/3), pp. 899–901, (1981).
Herrmann, et al.;-Synthesis-pp. 204–205, (1979).

*Primary Examiner*—Joseph Paul Brust
*Attorney, Agent, or Firm*—Sprung, Horn, Kramer & Woods

[57] ABSTRACT

Tertiary alkyl cyanides of the general formula

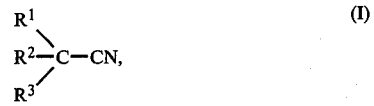

(I)

wherein
R¹, R² and R³ represent identical or different alkyl group or, together with the tertiary carbon atom to which they are bonded, form a polycycloalkyl group, or
R¹ and R², together with the tertiary carbon atom to which they are bonded, form a cycloalkyl group or a bicycloalkyl group, the alkyl groups, polycycloalkyl group, cycloalkyl group or bicycloalkyl group being optionally substituted by suitable substituents (as hereinbefore defined), are obtained in good yields by a process in which a tertiary alkyl halide of the formula

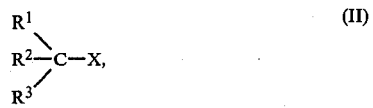

(II)

wherein
X represents a chlorine, bromine or iodine atom, and
R¹, R² and R³ have the meaning given above, is reacted with trimethylsilyl cyanide of the formula, (CH₃)₃SiCN (III), in the presence of a Lewis acid selected from SnCl₄, TiCl₄ and BiCl₃, and, if appropriate, in the presence of a diluent, at a temperature between 10° and 40° C. The tertiary alkyl cyanides of formula (I) can be used as intermediate products, for example for the preparation of known herbicides.

12 Claims, No Drawings

PREPARATION OF TERTIARY ALKYL CYANIDES

The invention relates to an unobvious process for the preparation of certain tertiary alkyl cyanides from the corresponding tertiary alkyl halides. The products of the process of the present invention can be used as intermediate products, for example for the preparation of known herbicides.

To our knowledge, no general process for the preparation of tertiary alkyl cyanides from the corresponding tertiary alkyl halides by exchange of the halogen for the nitrile group has hitherto been disclosed. While primary and secondary alkyl halides can be converted into the corresponding nitriles by condensation with alkali metal cyanides, the analogous reaction with tertiary alkyl halides is not possible. Thus, for example, amyl chloride can be converted, using sodium cyanide, into caproic acid nitrile in a maximum yield of 72%, after a reaction time of 96 hours; in contrast, secondary amyl chloride or bromide gives only 30% of nitrile, and tertiary amyl chloride or bromide yields no nitrile at all by this process (see Houben-Weyl, Methoden der Organischen Chemie (Methods of Organic Chemistry), 4th edition, volume VIII, page 293 (1952)). In the reaction of alkyl halides with heavy metal cyanides, such as silver or copper cyanide, the formation of the corresponding isonitriles is favoured, as is known (see, for example, Chem. Reviews 42, pages 189–283 (1948).

The present invention now provides a process for the production of a tertiary alkyl cyanide of the general formula

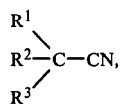

wherein
R¹, R² and R³ represent identical or different alkyl groups or, together with the tertiary carbon atom to which they are bonded, form a polycycloalkyl group, or
R¹ and R², together with the tertiary carbon atom to which they are bonded, form a cycloalkyl group or a bicycloalkyl group, the alkyl groups, polyalkyl group, cycloalkyl group or bicycloalkyl group being optionally substituted by suitable substituents (as hereinafter defined)
characterized in that a tertiary alkyl halide of the general formula

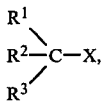

wherein
X represents a chlorine, bromine or iodine atom, and
R¹, R² and R³ have the same meanings given above,
is reacted with trimethylsilyl cyanide of formula $(CH_3)_3SiCN$ (III), in the presence of a Lewis acid selected from $SnCl_4$, $TiCl_4$ and $BiCl_3$, and, if appropriate, in the presence of a diluent, and, if appropriate, at a temperature between 10° and 40° C.

It is surprising that the process of the present invention allows compounds of formula (I) to be obtained in good yields.

The term "suitable substituent" as used herein means those substituents which do not deactivate the Lewis acid used. The following may be mentioned as examples of these substituents: cyano, fluorine and chlorine which is bonded to a primary carbon atom.

If tert.-butyl chloride is used as the starting material, tin tetrachloride as the Lewis acid and dichloromethane as the diluent, the course of the reaction according to the present invention is illustrated by the following equation:

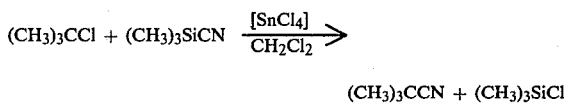

$$(CH_3)_3CCN + (CH_3)_3SiCl$$

Preferred tertiary alkyl halides of formula (II) to be used as the starting materials are those in which
R¹, R² and R³ independently represent an alkyl group having 1 to 10 carbon atoms or, together with the tertiary carbon atom to which they are bonded, represent a polycycloalkyl group having up to 20 carbon atoms: or
R¹ and R² additionally represent, together with the carbon atom to which they are bonded, a cycloalkyl group having 3 to 12 carbon atoms or a bicycloalkyl group having 6 to 10 carbon atoms, the alkyl group, polycycloalkyl group, cycloalkyl group or bicycloalkyl group being optionally substituted by suitable substitutents (as hereinbefore defined), and
X represents a chlorine, bromine or iodine atom.

Particularly preferred tertiary halides of formula (II) are those in which X represents a chlorine atom.

As is clear from the radical definitions, the expression "tertiary alkyl cyanides" and "tertiary alkyl halides" is to be understood, within the scope of this invention, as also meaning saturated cycloaliphatic halides and cyanides, in addition to the open-chain compounds, as well as certain substitution products of both basic types. The saturated cycloaliphatic halides and cyanide also include polycyclic alkyl halides and cyanides with the halogen atom or cyano group at the bridge head, for example the 1-halogenoadamantanes and 1-cyanoadamantanes.

Tertiary alkyl halides of formula (II) which can be used according to the invention are known and can be prepared according to known processes (see, for example, Houben-Weyl, Methoden der Organischen Chemie (Methods of Organic Chemistry), 4th edition, volume V/3, pages 503 et seq. (1960) and volume V/4, pages 13 et seq. (1962)). The following may be mentioned as examples: t-butyl chloride, t-amyl chloride, 1-chloro-1-methyl-cyclooctane, 1-chloro-1-propyl-cyclohexane, 2-chloro-2-methyl-[2.2.2]-bicyclooctane and 1-bromoadamantane. t-Butyl chloride is particularly preferred.

Trimethylsilyl cyanide of formula (III) is known, (see, for example, Synthesis 1979, pages 522 and 523, and also DE-OS (German Published Specification) 3,018,821).

The reaction according to the invention is preferably carried out in the presence of an inert solvent as the diluent. Certain chlorinated hydrocarbons, (which, of course, are not permitted to contain halogen bonded to tertiary carbon), such as, in particular, dichloromethane and 1,2-dichloroethane, are particularly suitable for this purpose.

If the reaction is carried out without a solvent, somewhat lower yields are generally obtained.

The reaction according to the invention is carried out in the presence of the specified Lewis acids, SnCl$_4$, TiCl$_4$ and BiCl$_3$, SnCl$_4$ being particularly preferably employed, since the highest yields are obtained with this compound.

The reaction temperatures are, in general, between 10° and 40° C., preferably between 15° and 25° C.; the reaction is most advantageously carried out at room temperature. In general, the process is carried out under normal pressure.

The reaction times are normally 24 to 38 hours.

In general, 1 to 1.8 mols, preferably 1.2 to 1.6 mols, of trimethylsilyl cyanide of formula (III) are employed per mol of tert.-alkyl halide of formula (II) in carrying out the process according to the invention.

The Lewis acid is employed in less than the stoichiometric amount, in general in an amount of 10–40 mol%, preferably of 20–30 mol%, relative to the compound of formula (II). Quantities of <10 mol% require relatively long reaction times, while equivalent (stoichiometric) quantities, in contrast, inhibit the reaction.

The reaction is desirably carried out with the exclusion of moisture and, in addition is advantageously also carried out under an inert gas atmosphere, most simply under nitrogen.

If the reaction is carried out using a diluent, it is advantageous initially to introduce the tert.-alkyl halide and the trimethylsilyl cyanide in the dry solvent, and to add the Lewis acid, under a nitrogen atmosphere.

However, it is also possible first to combine the trimethylsilyl cyanide and the Lewis acid, and only then to add the tert.-alkyl halide. If the reaction is carried out without a solvent, the latter mode of reaction is more suitable. Since the mixing of trimethylsilyl cyanide and SnCl$_4$ is slightly exothermic, the mixture should be allowed to cool in this case, and only then should the tert.-alkyl halide be added.

As a rule, the progress of the reaction can easily be monitored by $^1$H-NMR spectroscopy. For example, the signal of the tert.-butyl group of the tert.-butyl chloride gradually vanishes as the reaction proceeds, while the intensity of the signal of the tert.-butyl group of the pivalonitrile slowly increases at a somewhat higher field. (At a slightly higher field, a further singlet can be detected in this case. It is not clear whether this is a complexed form of the product; it is no longer found after the working-up process in aqueous medium).

The working-up process is effected in the customary manner (see the preparative examples hereinbelow), and the tertiary alkyl cyanides of formula (I) are finally isolated in the pure form by distillation or crystallization.

Some of the tertiary alkyl cyanides of formula (I) which can be prepared by the process according to the invention are known; these nitriles are valuable intermediate products, for example for the preparation of herbicides, tensides and anti-corrosion agents.

Thus, for example, pivalonitrile of formula (A) can be converted, by catalytic hydrogenation, into neopentylamine of formula (B), which can be reacted in various ways to give the known herbicidally active compound 1-amino-6-ethylthio-3-neopentyl-1,3,5-triazine-2,4(1H, 3H)-dione of formula (K) (see, for example, Danish Patent Specification No. 136,067):

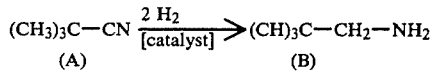

One route of the process proceeds via the following stages (see Belgian Patent Specification No. 682,820; Angew. Chem. 82 (1970), pages 63–67; and Synthesis 1970, pages 542–543; and DE-OS (German Published Specification) 2,254,200):

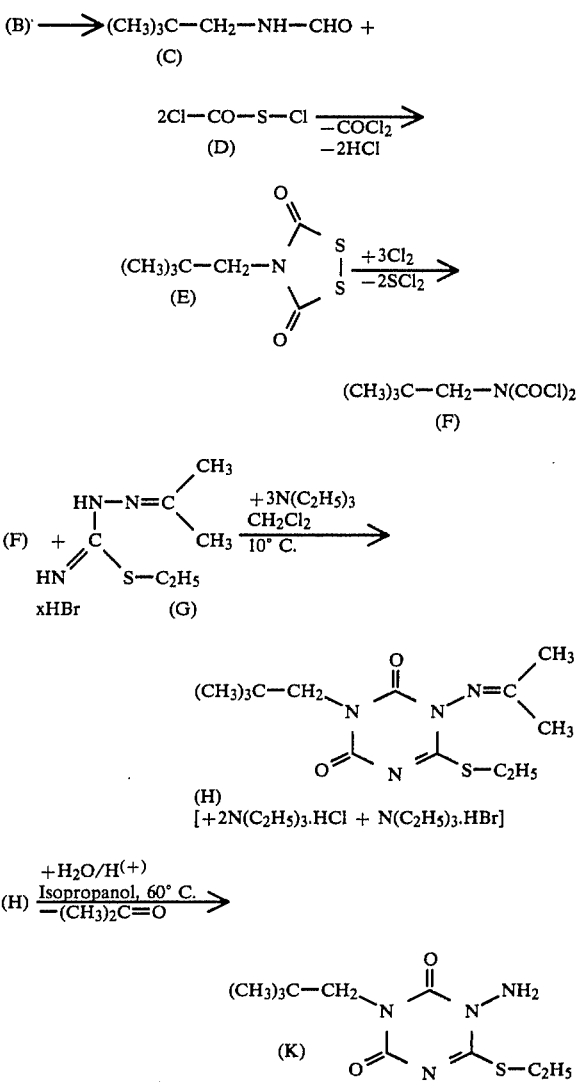

Another route of the process proceeds via the following stages (see DE-OS (German Published Specification) No. 3,006,226 and DE-OS (German Published Specification) No. 3,006,263):

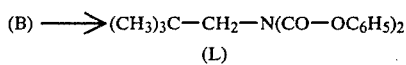

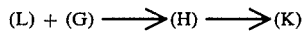

The preparative examples below serve further to illustrate the process of the present invention.

PREPARATIVE EXAMPLES

General Instructions for the Preparation of Tert.-alkyl Cyanides 30 mol% of $SnCl_4$ is added slowly, and while stirring, to a solution of 10 mmols of tert.-alkyl chloride and 15 mmols of trimethylsilyl cyanide in 30 ml of dry methylene chloride, at room temperature, under nitrogen. After 24 to 38 hours, the reaction solution (meanwhile almost black) is poured onto ice water and shaken vigorously. The organic phase is separated off, the aqueous phase is washed twice with methylene chloride and the combined organic phases are washed with 10% strength sodium bicarbonate solution. The solution is dried over sodium sulphate, concentrated and distilled.

The following Examples 1 to 12 were carried out as indicated in the foregoing general instructions using the starting materials of formula (I) and reaction times indicated in Table 1. The identity of the products of formula (I) of the process, yields and physical data on the products of the process are also evident from Table 1 below:

A similar procedure was followed for larger batches.

TABLE 1

| Example No. | Starting material (II) | Product (I) of the process | Reaction time (hours) | Yields (% of theory) by NMR*/isolated** | | Boiling point or melting point (mp) | Position of the $CH_3$ group of (I) in the NMR spectrum*** |
|---|---|---|---|---|---|---|---|
| 1 | $(CH_3)_3CCl$ | $(CH_3)_3CCN$ | 36 | ~75 | 64 | 105–7° C. | 1.3 |
| 2 | $(CH_3)_2CCl$ \| $C_2H_5$ | $(CH_3)_2CCN$ \| $C_2H_5$ | 38 | 80 | 75 | 32° C./25 mbars | 1.3 |
| 3 | cyclopentyl-$CH_3$/Cl | cyclopentyl-$CH_3$/CN | 32 | 75 | 67 | 52° C./25 mbars | 1.3 |
| 4 | $n\text{-}C_5H_{11}$—C($CH_3$)($CH_3$)—Cl | $n\text{-}C_5H_{11}$—C($CH_3$)($CH_3$)—CN | 38 | 78 | 70 | 72° C./25 mbars | 1.3 |
| 5 | $(CH_2)_{11}$ C($CH_3$)(Cl) | $(CH_2)_{11}$ C($CH_3$)(CN) | 38 | 75 | 60 | mp 158–162° C. | 1.3 |
| 6 | $Cl\text{—}(CH_2)_3$—C($CH_3$)($CH_3$)—Cl | $Cl\text{—}(CH_2)_3$—C($CH_3$)($CH_3$)—CN | 25 | 85 | 72 | 90° C./25 mbars | 1.3 |
| 7 | cyclohexyl-$CH_3$/Cl | cyclohexyl-$CH_3$/CN | 25 | 85 | 76 | 82° C./25 mbars | 1.3 |
| 8 | cyclopentyl-$C_2H_5$/Cl | cyclopentyl-$C_2H_5$/CN | 26 | 87 | 82 | 67° C./25 mbars | 1.1 (triplet) |
| 9 | norbornyl-Cl/$CH_3$ | norbornyl-CN/$CH_3$ | 24 | 90 | 84 | 85° C./25 mbars | 1.4 |
| 10 | $n\text{-}C_6H_{13}$—C($CH_3$)($Cl$)—$C_4H_9\text{-}n$ | $n\text{-}C_6H_{13}$—C($CH_3$)($CN$)—$C_4H_9\text{-}n$ | 25 | 80 | 70 | 54° C./0,665 mbars | 1.3 |
| 11 | cycloheptyl-$CH_3$/Cl | cycloheptyl-$CH_3$/CN | 38 | 60 | 44 | 62° C./25 mbars | 1.3 |
| 12 | Br-adamantyl (1-bromo-) | CN-adamantyl (1-cyano) | 30 | 38 | 29 | 194° C. | — |

TABLE 1-continued

| Example No. | Starting material (II) | Product (I) of the process | Reaction time (hours) | Yields (% of theory) by NMR*/isolated** | Boiling point or melting point (mp) | Position of the CH3 group of (I) in the NMR spectrum*** |
|---|---|---|---|---|---|---|
| | adamantane | adamantane | | | | |

*measured by ¹H—NMR spectroscopic analysis
**yield of isolated product
***¹H—NMR spectrum (in CCl₄; tetramethylsilane (TMS) as the internal standard)

It will be appreciated that the instant specification and examples are set forth by way of illustration and not limitation, and that various modifications and changes may be made without departing from the spirit and scope of the present invention.

We claim:

1. A process for the preparation of a tertiary alkyl cyanide of the formula

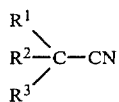

in which
R¹, R² and R³ each independently is an alkyl group or, together with the tertiary carbon atom to which they are bonded, form a polycycloalkyl group, or
R¹ and R², together with the tertiary carbon atoms to which they are bonded, form a cycloalkyl group or a bicycloalkyl group,
comprising reacting a tertiary alkyl halide of the formula

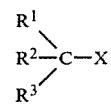

in which
X is a chlorine, bromine or iodine atom, with trimethylsilyl cyanide of the formula (CH₃)₃SiCN in the presence of a Lewis acid selected from the group consisting of SnCl₄, TiCl₄ and BiCl₃.

2. A process according to claim 1, wherein the reaction is carried out at a temperature between about 10° and 40° C.

3. A process according to claim 1, wherein about 1 to 1.8 mols of trimethylsilyl cyanide are employed per mol of tertiary alkyl halide.

4. A process according to claim 1, wherein about 10 to 40 mol% of the Lewis acid is employed per mol of tertiary alkyl halide.

5. A process according to claim 1, wherein SnCl₄ is employed as the Lewis acid.

6. A process according to claim 1, wherein the reaction is carried out in the presence of a diluent.

7. A process according to claim 6, wherein the diluent is a chlorinated hydrocarbon free from chlorine bonded to a tertiary carbon atom.

8. A process according to claim 6, wherein dichloromethane or 1,2-dichloroethane is used as the diluent.

9. A process according to claim 1, in which
R¹, R² and R³ each independently is an alkyl group having 1 to 10 carbon atoms, or, together with the tertiary carbon atoms to which they are bonded, form a polycycloalkyl group having up to 20 carbon atoms; or
R¹ and R² together with the carbon atom to which they are bonded, form a cycloalkyl group having 3 to 12 carbon atoms or a bicycloalkyl group having 6 to 10 carbon atoms.

10. A process according to claim 1, wherein the tertiary alkyl halide is a tertiary alkyl chloride.

11. A process according to claim 1, wherein the tertiary alkyl halide is tert.-butyl chloride.

12. A process according to claim 11, wherein about 1.2 to 1.6 mols of trimethylsilyl cyanide and 20 to 30 mol % of the Lewis acid are employed per mol of tertiary alkyl halide, SnCl₄ is employed as the Lewis acid, and the reaction is carried out at about 15° to 25° C. in the presence of dichloromethane or 1,2-dichloroethane as diluent.

* * * * *